(12) United States Patent
Larsen

(10) Patent No.: US 10,722,283 B2
(45) Date of Patent: Jul. 28, 2020

(54) APPARATUS FOR THERMAL ABLATION

(71) Applicant: LiNA Medical ApS, Glostrup (DK)

(72) Inventor: Steffen Hovmand Larsen, Rodovre (DK)

(73) Assignee: LINA MEDICAL APS, Glostrup (DK)

( * ) Notice: Subject to any disclaimer, the term of this patent is extended or adjusted under 35 U.S.C. 154(b) by 495 days.

(21) Appl. No.: 15/528,343

(22) PCT Filed: Nov. 23, 2015

(86) PCT No.: PCT/EP2015/077372
§ 371 (c)(1),
(2) Date: May 19, 2017

(87) PCT Pub. No.: WO2016/079340
PCT Pub. Date: May 26, 2016

(65) Prior Publication Data
US 2017/0319254 A1    Nov. 9, 2017

(30) Foreign Application Priority Data

Nov. 21, 2014   (DK) .................................. 2014 70727

(51) Int. Cl.
*A61B 18/00* (2006.01)
*A61B 18/04* (2006.01)
*A61B 90/00* (2016.01)

(52) U.S. Cl.
CPC ..... *A61B 18/04* (2013.01); *A61B 2018/00005* (2013.01); *A61B 2018/0022* (2013.01); *A61B 2018/00559* (2013.01); *A61B 2018/00577* (2013.01); *A61B 2018/00791* (2013.01); *A61B 2018/046* (2013.01); *A61B 2090/0813* (2016.02)

(58) Field of Classification Search
CPC ............ A61B 18/04; A61B 2018/0022; A61B 2018/00559; A61B 2018/00791; A61B 2018/046; A61B 17/12136; A61B 17/12131; A61B 2090/814; A61B 2090/037

See application file for complete search history.

(56) References Cited

U.S. PATENT DOCUMENTS 5,120,316 A * 6/1992 Morales ............ A61M 25/0075
                                                      604/148
5,248,312 A * 9/1993 Langberg ............... A61B 17/22
                                                       606/27

(Continued)

FOREIGN PATENT DOCUMENTS

CN          1787790 A       6/2006
CN        102711640 A      10/2012
(Continued)

*Primary Examiner* — Linda C Dvorak
*Assistant Examiner* — Annabeth E Rodriguez
(74) *Attorney, Agent, or Firm* — Muncy, Geissler, Olds & Lowe, P.C.

(57) ABSTRACT

An apparatus for treating uterine disorders by effecting necrosis of the uterine endometrium. The apparatus has a catheter with a bladder which can be inflated with a hot medium. To prevent early inflation of the bladder, the apparatus has an occlusion member arranged between a reservoir which contains the inflation medium and the bladder.

13 Claims, 8 Drawing Sheets

(56) References Cited

U.S. PATENT DOCUMENTS

| | | | |
|---|---|---|---|
| 5,800,493 A * | 9/1998 | Stevens | A61B 18/08 606/28 |
| 2003/0055470 A1 | 3/2003 | Mon et al. | |
| 2008/0147056 A1* | 6/2008 | van der Weide | A61B 18/18 606/33 |
| 2010/0100091 A1 | 4/2010 | Truckai | |
| 2013/0296837 A1 | 11/2013 | Burnett et al. | |
| 2015/0126990 A1 | 5/2015 | Sharma et al. | |

FOREIGN PATENT DOCUMENTS

| | | |
|---|---|---|
| WO | WO99/60960 | 12/1999 |
| WO | WO00/00100 | 1/2000 |
| WO | WO2014/195490 A1 | 12/2014 |

* cited by examiner

APPARATUS FOR THERMAL ABLATION

BACKGROUND OF THE INVENTION

Field of the Invention

The invention relates to an apparatus for thermal ablation at a site in a subject. Particularly, the invention relates to an apparatus for treating uterine disorders by effecting necrosis of a uterine endometrium by use of a distendable bladder which is inserted into the uterus.

Brief Description of the Related Art

Application of thermal energy is known for treating body tissues and for causing necrosis. Particularly, it is well known to effect necrosis of the endometrium e.g. by use of an expandable bladder or a bladder which is filled with an inflation medium at an elevated temperature, herein referred to as necrosis temperature, typically about 80-90° Celsius.

In an unexpanded state, the bladder is inserted into uterus of the subject and a hot inflation medium is displaced into the bladder which thereby expands. Close contact between the hot outer surface of the bladder and the tissue lining for which necrosis is desired is maintained typically for 8-15 minutes after which the inflation medium is drained from the bladder. The collapsed bladder can finally be removed from the subject.

The inflation medium may be stored in a reservoir from which it can be displaced into the bladder. The reservoir can contain heating means for obtaining the necrosis temperature.

Under certain conditions, the bladder may expand prior to the treatment, e.g. in the bladder. Such an unwanted expansion may be due to handling, transport, or manufacturing conditions. Particularly, the bladder may expand due to thermal expansion of the inflation medium e.g. if the apparatus is stored in a warm place, or if the manufacturing process involves hot processes. If the bladder expands outside uterus prior to the treatment, it may become difficult or impossible to insert the bladder through the narrow cervix and the apparatus may potentially be unusable.

BRIEF SUMMARY OF THE INVENTION

It is an object of embodiments of the invention to improve the existing methods and apparatuses for conducting thermal ablation and particularly to provide a reliable apparatus which facilitates insertion of the bladder through the cervix and eliminates or reduces the risk of early expansion of the bladder outside uterus.

It is a further object to increase the safety and to prevent use of the apparatus with unsuitable temperatures, i.e. to increase the safety and ensure a correct minimum temperature.

It is a further object to facilitate manufacturing, and particularly to enable a simpler and potentially cheaper way of manufacturing an apparatus for thermal ablation.

According to a first aspect, the invention provides an apparatus for treating uterine disorders by effecting necrosis of a uterine endometrium, the apparatus comprising:
 a catheter having a proximal end and a distal end;
 a bladder attached to the proximal end for insertion into uterus and being distendable upon introduction of an inflation medium;
 a reservoir containing the inflation medium;
 heating means configured to heat the inflation medium to a necrosis temperature; and
 inflation means being operative for moving the inflation medium between the storage means and the bladder;

According to the invention, the apparatus further comprises a removable occlusion member arranged between the reservoir and the bladder to prevent flow of the inflation medium from the reservoir to the bladder.

Due to the occlusion member, the flow of the inflation medium can be controlled more precisely and early inflation can be prevented. Before use, e.g. immediately before use, the occlusion member is removed and the flow of the inflation medium from the reservoir to the bladder is enabled.

The surgeon may e.g. wait until the inflation medium has reached the necrosis temperature and remove the occlusion member immediately before or even after the bladder is inserted into the uterus.

Due to the occlusion member, the bladder may be kept in a low pressure condition where the size of the bladder is reduced by compression due to a pressure difference across the wall of the bladder. Accordingly, the occlusion member facilitates a very small, compressed, configuration of the bladder until it is expanded inside the uterus. The small, compressed size and shape of the bladder increases the user comfort and reduces the pains sometimes experienced upon insertion of the bladder through cervix.

Thermal expansion is the tendency of matter to change volume in response to a change in temperature. Due to the heating of the inflation medium, the medium expands and the pressure therefore increases. Due to the occlusion member, an unintended, early, inflation of the bladder caused by thermal expansion can be avoided.

The occlusion member further enables separate manufacturing of the bladder and the reservoir. During manufacturing, the inflation medium is safely maintained in the reservoir even though the bladder is not yet attached. This makes manufacturing more flexible and potentially cheaper.

Herein the term necrosis temperature is that temperature at which the apparatus is intended to carry out the tissue necrosis. The temperature may vary—some apparatuses according to the invention may use a necrosis temperature in the range of 80-100 degrees, others may use a higher temperature, e.g. in the range of 120-140 degrees or even higher.

Herein removable means that the occlusion member at least can be changed, moved, melted, ruptured, destroyed or in any other way manipulated in such a way that the prevention of flow of the inflation medium from the reservoir to the bladder disappears. I.e. removal of the occlusion member brings the apparatus to a state where the bladder can be inflated by moving the inflation medium from the reservoir to the bladder.

In one example, the occlusion means forms part of a valve structure and is removable by actuation of the valve. In another example, the occlusion means is destroyable by a predefined operation, e.g. a pull in a handle, or by operation of the inflation means etc.

The occlusion member may be configured to be removed at a specific temperature of the inflation medium. For that purpose, the occlusion member may particularly be in thermal communication with the inflation medium and configured to be triggered by the temperature thereof. This facilitates automatic removal of the occlusion member during heating of the inflation medium, and the user may therefore use the apparatus without considering removal of the occlusion member.

In one embodiment, the occlusion member is configured to melt based on the increasing temperature of the inflation medium, e.g. at a melting temperature which is lower than the necrosis temperature. During heating of the inflation medium, the occlusion member simply melts away and opens a passage between the reservoir and the bladder.

The occlusion member may e.g. be made from a polymer material or from wax, e.g. having a melting point between 40 and 120 degrees depending on the necrosis temperature for which the apparatus is made.

The melting temperature could be at least 10, 20, 30 or 40 degrees lower than the necrosis temperature such that the occlusion member is melted completely when the necrosis temperature is reached and the treatment can start. Particularly, the melting point is balanced with the speed by which the temperature of the inflation medium increases in such a way that the occlusion member is completely melted between 2 and 60 seconds before the necrosis temperature is reached or at least completed in less than 100 seconds.

The apparatus may particularly be sterilised by a process causing the apparatus to reach an elevated sterilisation temperature. The sterilisation process could e.g. be a steam sterilisation process, electro-beam sterilisation, or Gas-ethylene sterilisation etc. These processes typically include an increased temperature of the sterilised subject. In this case, the apparatus according to the invention may particularly comprise an occlusion member made such that it melts at a temperature which is higher than the temperature required by, or caused by the sterilisation process. In that way, it is prevented that the bladder can start deflation already during manufacturing once the apparatus is sterilised, and it is prevented that the occlusion member is damaged by the sterilisation causing a potential leaking of the inflation medium into the bladder before the intended use.

The melting temperature may preferably be between the sterilisation temperature and the necrosis temperature. It could e.g. be at least 20 degrees higher than the sterilisation temperature and/or 20 degrees colder than the necrosis temperature.

In one example, the apparatus is made for a necrosis temperature of 140-145 degrees Celsius and is sterilised by gas-ethylene sterilisation which could increase the temperature to e.g. 50-55 degrees Celsius. In this case, the melting point of the occlusion member is preferably between 55 and 140 degrees Celsius.

The occlusion member could be made from, or it may include a material which is meltable, e.g. from a material selected from the group consisting of paraffin, wax, polyethylene (PE), EVA, PVP, polyurethane (PU), and different sorts of starch including natural occurring starch such as potato or maize starch. As will be discussed further, the occlusion member may have a low water permeability, e.g. sufficiently low to prevent water absorption in glycerol in the reservoir from the bladder. The water transmission coefficient from bladder to reservoir may particularly be below 0.1 gram such as g per day (24 hours) measured at 60 percent relative humidity at 20 degrees C. The occlusion member may particularly have a content of at least 25 percent such as at least 28 percent of EVA. It could e.g. be made from Elvax® EVA Copolymer Resin from DuPont, e.g. Elvax 220 W.

The occlusion member is preferably of a material with a high melt flow index, in order to provide that the occlusion member is sufficiently melted before the procedure starts.

The occlusion member could be configured to be ruptured, destroyed or moved by the inflation means such that interaction between the inflation means and the occlusion member during operation of the inflation means opens a passage between the bladder and the reservoir.

The apparatus may comprise a tube, e.g. a polymer tube, forming fluid communication between the reservoir and the bladder. In this embodiment, the occlusion member forms a separate element inserted into the tube. The occlusion member may particularly be a soft and elastically deformable element which can be inserted into the tube and which seals the passage by use of its elastic properties by which the occlusion member may be elastically compressed into the tube. The sealing effect may also be obtained by at least partly or completely adhesive properties, e.g. by use of a soft and adhesive polymer for the inner wall of the tube and/or for the outer surface of the occlusion member.

The occlusion member may form an elongated element e.g. having an oblong sidewall tapering towards an end. Particularly, this occlusion member may have a cavity enabling easy elastic deformation of the sidewall for insertion into the tube.

The occlusion member may be formed of a film-like material applied around the end of the tube in order to seal the passage.

The occlusion member could be removable by manual activation of a control. This feature could be used with or without the feature of a melting occlusion member. With the occlusion member, the manual activation of a control can be used, e.g. if the occlusion member does not melt, e.g. if the apparatus is operated at a low temperature. Without the melting occlusion member, the manual activation can form an alternative way of operating the apparatus—i.e. in an embodiment where the occlusion member is not supposed to melt. In one embodiment, the practitioner is supposed to initiate the treatment by removing the occlusion member. Compared with the embodiment where the occlusion member melts this gives the practitioner exact knowledge about when the passage to the bladder is opened. If the practitioner forgets to open the passage manually, the melting properties may ensure removal once the inflation medium is heated.

The pressure in the bladder may be negative to thereby facilitate a slim shape of the bladder and thereby easy insertion. The pressure in the bladder may e.g. be maintained at a pressure below the surrounding atmospheric pressure until the occlusion member is removed. As an example, the pressure could be less than 0.9 bar such as less than 0.8 bar or less than 0.7 bar, or simply sufficiently low to always be lower than the atmospheric pressure.

The inflation means may be configured to move the inflation medium between the storage means and the bladder at a pressure which exceeds a burst pressure by which the occlusion member is removed by bursting. In this way, the occlusion member is effectively removed by use of the inflation means. This procedure may e.g. be combined with the aforementioned melting of the occlusion member.

According to a second aspect, the invention provides a method of sterilising an apparatus for treating uterine disorders by effecting necrosis of a uterine endometrium, the apparatus comprising:

a catheter having a proximal end and a distal end;
    a bladder attached to the proximal end for insertion into uterus and being distendable upon introduction of an inflation medium;
    a reservoir containing the inflation medium;
    heating means configured to heat the inflation medium to a necrosis temperature;
    inflation means being operative for moving the inflation medium between the storage means and the bladder; and
    an occlusion member which melts at a melting temperature which is lower than the necrosis temperature and which is arranged between the reservoir and the bladder to prevent flow of the inflation medium from the reservoir to the bladder;

the method comprising the steps of sterilising the apparatus by use of a process causing the apparatus to reach a sterilisation temperature which is lower than the melting temperature.

According to a third aspect, the invention provides a method of preparing an apparatus for carrying out tissue necrosis of a subject, e.g. of a uterus, the method comprising the step of providing an apparatus according to the claims, heating the inflation medium, and melting the occlusion member by use of the heated inflation medium.

For easy insertion of the bladder, it may be an advantage to provide the apparatus in a completely deflated state and preferably a state where the pressure in the bladder is lower than the surrounding pressure and particularly lower than the pressure in the reservoir. This is possible by use of the occlusion member which can seal the bladder once the pressure is reduced.

The apparatus may include control means for electronically controlling the treatment by operation of the heater and the inflation means and by communication with various sensors, e.g. for sensing the pressure and/or the temperature. In this embodiment, the apparatus may be configured to provide an alert if a specific temperature and/or pressure corresponding to a temperature and/or pressure necessary to remove the occlusion member, has not been reached.

The apparatus may e.g. comprise temperature detection means arranged to detect the temperature of the inflation medium, and the control means may be configured to inform the user when the melting temperature of the occlusion member is reached.

The pressure and/or temperature of the inflation medium could be detected, e.g. continuously or in discrete steps, e.g. both in the reservoir and in the bladder. In that way, the apparatus may detect when the occlusion member melts and the apparatus may warn the user if it is not yet melted when the treatment is ready to begin.

The control means may include an electronic circuit, e.g. having memory means with a predefined pressure and/or temperature range stored therein and indicating a desired pressure and/or temperature in the bladder during heating for the purpose of removing the occlusion member, and optionally also during a subsequent treatment of the patient.

The pressure and/or temperature range may specify at least a minimum and a maximum pressure/temperature during the heating process and/or during the treatment. Until reaching the minimum pressure, the inflation means is operated in a positive direction to continue increasing the pressure, and when reaching the maximum pressure, the inflation means is operated in the negative direction until the pressure becomes below the maximum pressure. Until reaching the minimum temperature, the heating means is operated to increase the temperature and when reaching the maximum temperature, heating is stopped.

In one embodiment, the control means is configured to use a combination between temperature and pressure to determine when the occlusion member is removed. E.g. by evaluating the increase in pressure upon operation of the inflation means upon reaching a specific temperature of the inflation medium. The control means may be configured for a predefined sequence to effect a pre-defined treatment—e.g. including the following steps:

a) The inflation medium is heated e.g. with simultaneous pressure correction by operation of the deflation means; The first step is typically carried out before the bladder is inserted into the uterus.
b) When the inflation medium is heated, the control means may provide a ready signal indicating that the occlusion member is melted, and that the bladder may now be inserted in the uterus and that the ablation can therefore begin; For this purpose, the inflation means may be "test operated" during surveillance of the pressure in at least one of the reservoir and bladder.
c) The inflation means is operated in the positive direction to inflate the bladder; before this second step, the control means may wait for an activation signal to be given by the user. For this purpose, the apparatus may include a button or similar control for starting the process when the bladder is inserted into the uterus.
d) The pressure in the bladder is maintained during a pre-defined period of time;
e) The inflation means is operated in the negative direction to deflate the bladder; and
f) Finally, a finish signal indicating deflation of the bladder is transmitted and the bladder can be removed from the uterus.

Particularly, the reservoir may contain a larger amount of the inflation medium than what is necessary for inflating the bladder. In this embodiment, the heating means may be configured to heat the entire amount of the inflation medium, and the repeated deflation and inflation of the bladder may cause mixing of that portion of the inflation medium which is in the bladder with that portion of the inflation medium which is in the reservoir. As a result of the repeated deflation and inflation of the bladder, the bladder may become reheated several times during the treatment, and a more constant high temperature of the surface of the bladder can be obtained.

The reservoir may be formed by the inflation means itself—i.e. the reservoir may form a chamber of a pump which is used for inflating the bladder.

The inflation means may particularly be configured for operation in a negative direction both for obtaining a negative pressure in the reservoir, and in a positive direction for obtaining a positive pressure in the reservoir. The negative pressure may e.g. be used for moving the occlusion member out of the catheter and into the reservoir. The operation may therefore be initiated by operation in the negative direction for removing the occlusion member and followed by operation in the positive direction for inflating the bladder.

The inflation means may particularly be driven by power driven means and it may constitute a power driven pump, e.g. a displacement pump, or a centrifugal pump. The pump may e.g. form the structure of a syringe or the structure of a peristaltic pump etc. The apparatus may further comprise motor control means configured to determine a power consumption of the inflation means. The previously mentioned step f) of transmitting a finish signal may be triggered by detection of increased power consumption which will typically occur when the power driven pump reaches an endstop.

The use of a power driven syringe facilitates in a simple manner, an exact displacement of the inflation medium into the bladder and thus controlled expansion of the bladder.

The power driven means may work on the cylinder or on the piston to move that element relative to the other element of the syringe structure. The syringe structure also effectively forms the aforementioned reservoir whereby the inflation means itself forms the reservoir.

The syringe or piston may e.g. be directly connected to the occlusion member such that the occlusion member is moved, destroyed, or generally manipulated by the relative movement between piston and cylinder and thereby open the passage between the reservoir and the bladder.

Particularly, the combination between power driven means and a syringe structure enables precise dosing of the inflation medium into the bladder by use of very simple and cheap motors. Relative displacement of the cylinder and piston may e.g. be effected by a worm shaft etc. or it may generally be based on a threaded engagement between a driven and a driving element, e.g. between a nut which is rotated by the motor and therefore constitutes the driving element and a threaded piston or threaded element connected to the piston and which thereby constitutes the driven element.

Additionally, the combination between power driven means and a syringe structure enables stronger forces to work on the occlusion member for opening the passage between the reservoir and the bladder.

The power driven means used for driving the inflation means could particularly be constituted by a rotary motor of the kind including a rotor and a stator, e.g. a DC motor. Alternatively or additionally, the power driven means may include electromechanical actuation means, e.g. in the form of a solenoid operating e.g. to move a piston and cylinder relative to each other.

The apparatus may particularly be independently powered. Herein, independent powering means that the apparatus contains a local source of electrical energy, in the following simply referred to as a battery.

By the term "battery" is herein meant a number of cells, e.g. 1, 2, 3, 4 or more cells, each capable of delivering electrical power. Particularly, the battery may comprise at least one electrochemical cell and/or at least one capacitor.

The battery may typically deliver between 3 and 20 volt and have about 500-2600 mAH of capacity. It may be for disposable, one time, usage or it may be rechargeable for multiple usages.

Particularly, it is an object to make a completely independent, single piece apparatus, e.g. for single use. Typically, however, batteries should be disposed in containers specifically for receiving batteries, and typically, instruments which may have been contaminated with biological material, such as blood and tissue, should be disposed in other containers specifically for that purpose. It may therefore be an advantage if the apparatus comprises a detachable independent powering means designed for intended destruction by which the battery, capacitor, or similar power source becomes detached from the chassis such that reassembly becomes difficult or impossible.

To make a completely independent apparatus, not only power but also all other necessary elements may be included in a single piece apparatus. Accordingly, the apparatus may be formed by a single entity or component which comprises all the claimed features including the inflation medium and the inflation means such that a separate supply of the inflation medium becomes unnecessary.

The bladder may be pre-shaped e.g. to approximate the bicornual shape of the uterus. It may be manufactured from a bio-compatible, non-allergenic material, and it may come in different sizes, e.g. in two pre-shaped sizes; one for nulliparous uteri and one for parous uteri. The bladder may also have completely different shapes for non-endometrial bladder ablation.

The bladder could be made from an elastically deformable rubber, silicone or latex material. In one embodiment, the bladder comprises at least a first and a second bladder positioned one within the other to increase safety if one bladder should be ruptured.

In one particular embodiment, the bladder comprises a first and a second bladder, one within the other, and the inflation medium is injectable between the two bladders, i.e. the space between the first and second bladder forms a reservoir for the heated inflation medium while the inner bladder could be filed with an alternative inflation medium, e.g. in an unheated state.

In this embodiment, the inner bladder may e.g. be expanded by air. Since it is only the space between the first and second bladder which is filled with the heated inflation medium, the amount of heated inflation medium which is necessary for a treatment can be reduced whereby the thermal capacity of the system is reduced. This reduces also the necessary thermal energy for bringing the inflation medium to the requested temperature and the time it takes to heat the inflation medium. As a further advantage, the inflation medium cools down faster and the risk of unintended burns can be reduced.

The heating means may e.g. be incorporated in, or it may form part of the inflation means. Particularly, the heating means may form part of the previously described cylinder or piston. In this way, relative movement between the cylinder and piston also causes relative movement between the heating means and one of the cylinder and piston. This may increase the thermal convection and facilitate a more homogeneous temperature of the inflation medium.

The inflation medium may particularly be heated to a temperature above 100° C. and more particularly to a temperature above 130° C. such as to a temperature in the range of 120-150° C. To reach this temperature, the inflation medium may particularly be a liquid with a boiling point above 150° C. and preferably even above 200° C. The inflation medium may particularly be glycerol, e.g. $C_3H_8O$.

Glycerol is a liquid, which absorbs water with high affinity. Particularly in connection with glycerol, one problem may relate specifically to water absorption. The bladder is normally relatively thin, e.g. below 0.1 mm or even below 0.05 mm. The thin wall introduces a risk of absorbing water through the bladder into the glycerol. According to the invention, this may effectively be prevented by the occlusion member. Accordingly, the occlusion member may particularly prevent or reduce water permeation through the catheter into the reservoir, and it may thus effectively prevent absorption of water in the glycerol. Water in the glycerol lowers the boiling point and thereby increases the risk of unintended early distension of the bladder, e.g. during sterilisation.

For this reason, the occlusion member may not only seal leakage tight between the reservoir and the bladder, it may also have a low water permeability e.g. less than 0.1 or less than 0.01 gram of $H_2O$ in 24 hours measured at 20 degrees Celsius.

Further, the bladder may desirably be made from a material which resists temperatures above 150° C., or above 200° C., and desirable be made from a material which exposes at most 5 percent change in module of elasticity during a temperature increase from 20° C. to 150° C., where the module of elasticity is defined as a tendency of the material to be deformed elastically (i.e., non-permanently) when a force is applied to it.

The apparatus may comprise visual indication means indicating to the user that the occlusion member is already melted or in other ways removed. In that way, the user can see that the apparatus has been used and avoid reuse of a single use apparatus.

To ensure only one-time usage of the apparatus and disposal of the apparatus after use, the control means may be configured to only allow one single treatment after which the apparatus stops working.

The apparatus may comprise separate sensors for sensing temperature and pressure. The apparatus may also comprise several sensors capable of sensing temperature and/or several sensors capable of sensing pressure, and control logic capable of reading several pressure and/or temperature signals from the sensors and to determine a fault situation in case the difference between the signals from two identical sensors is above a limit value.

The catheter, the bladder, the inflating means, the heating means, and the control means could be joined inseparably to form integral parts of a mobile unit.

By mobile unit is herein meant a unit which does not need external power, i.e. it is powered by a battery or similar internally contained power source and it has a size, shape, and weight enabling it to be manipulated as a one-piece apparatus and by hand.

The mobile unit may, in one end form a handle suitable for manipulation of the unit by hand, and the catheter and bladder may form an opposite end of the mobile unit.

Before removal of the bladder from uterus, the bladder is deflated by removal of the inflation medium.

For this purpose, the inflation medium may be completely sealed in the reservoir to prevent entrance of air during deflation of the bladder.

The complete sealing of the inflation medium may ensure complete emptying and collapsing of the bladder and thus more simple removal of the bladder from the uterus after the treatment is finished.

The term Completely sealed herein means that the reservoir is liquid and gas tight enough to prevent intrusion of air during when the bladder is emptied. In one embodiment, the reservoir comprises no openings into the internal space inside the reservoir, and in another embodiment, the reservoir only comprises openings which can be sealed in a liquid or gas tight manner.

DETAILED DESCRIPTION OF AN EMBODIMENT

Further scope of applicability of the present invention will become apparent from the following detailed description and specific examples. However, it should be understood that the detailed description and specific examples, while indicating preferred embodiments of the invention, are given by way of illustration only, since various changes and modifications within the scope of the invention will become apparent to those skilled in the art from this detailed description.

Figure 1:
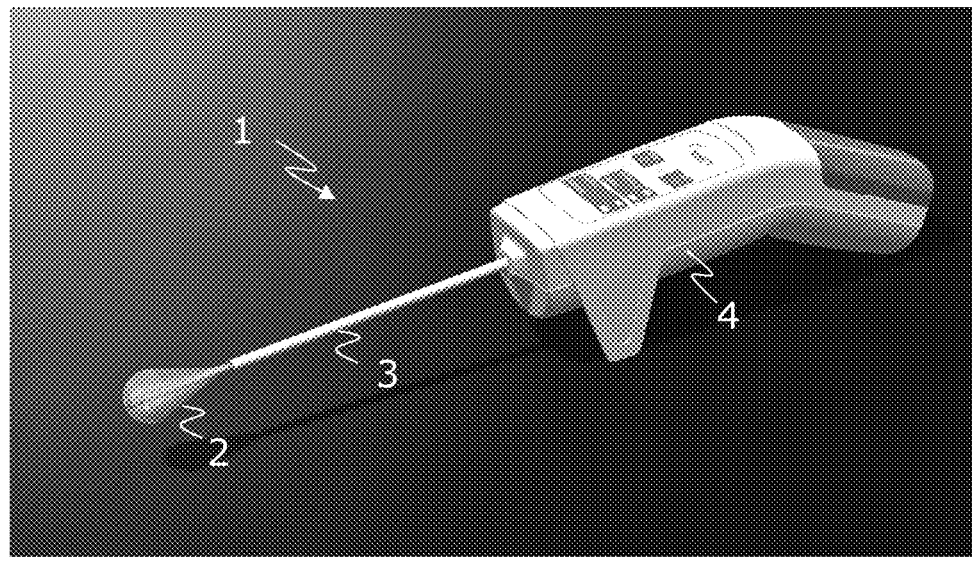
FIGS. 1 and 2 are perspective views of an assembled apparatus according to the invention.
Figure 2:
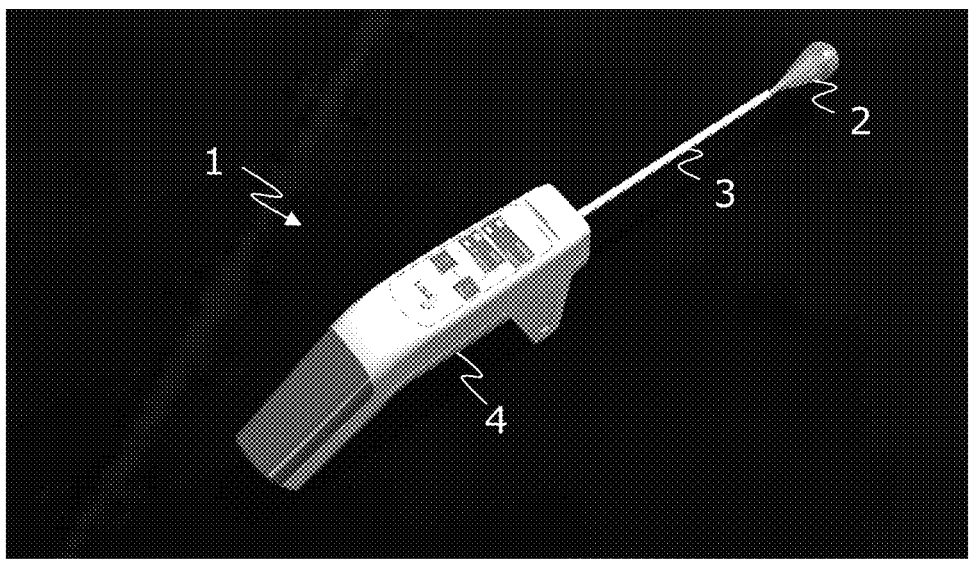

FIGS. 1 and 2 illustrate an apparatus for effecting necrosis of the endometrium. The apparatus further comprises an expandable bladder 2 which is connected to the reservoir by an elongated catheter 3. The reservoir is housed within the casing 4. The reservoir forms part of a displacement chamber forming the inflation means.

Figure 3:
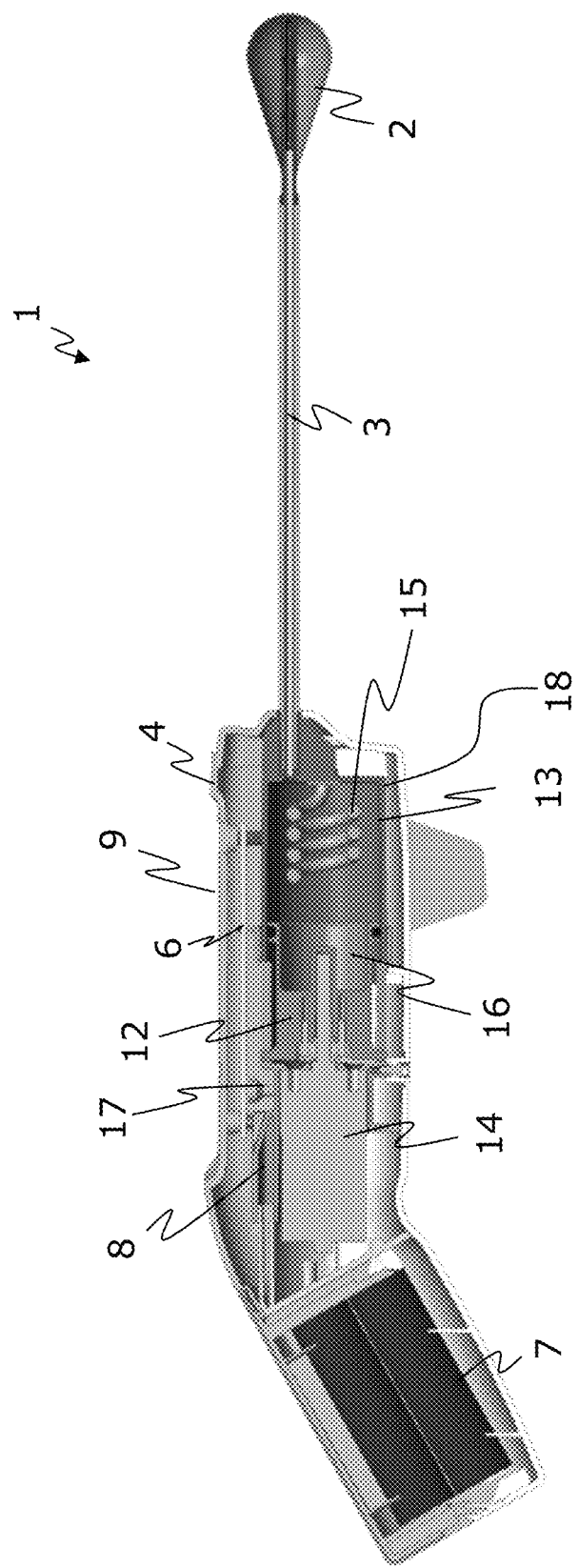
FIG. 3 is a side view, in cross section, of an apparatus according to the invention.

FIG. 3 illustrates the casing is in a cross sectional view in FIG. 3. The casing further houses a printed circuit board (PCB) 6, a battery 7, a body 8.

The displacement chamber is constituted by a syringe structure including a piston 12 movable in a cylinder 13 by an electrical motor 14—in this case a DC servo motor or step-motor.

The heating means 15 is attached to, and extends inside the cylinder 13. The piston forms a cavity 16 shaped and dimensioned to receive the heating means 15.

When the piston is moved in the cylinder, the heating means becomes received in the cavity and the inflation medium therefore becomes displaced or "stirred" in the chamber in the vicinity of the heating means 15. This increases the thermal convection and provides a more equal temperature in the inflation medium.

The apparatus further comprises a sensor 17 capable of sensing pressure and a sensor 18 capable of sensing temperature of the inflation medium in the bladder. The sensors communicate with the control means 9 and can be used for determining when the temperature has reached the melting point of the occlusion member and when the pressure in the bladder increases, i.e. when the occlusion member is removed.

Figure 4:
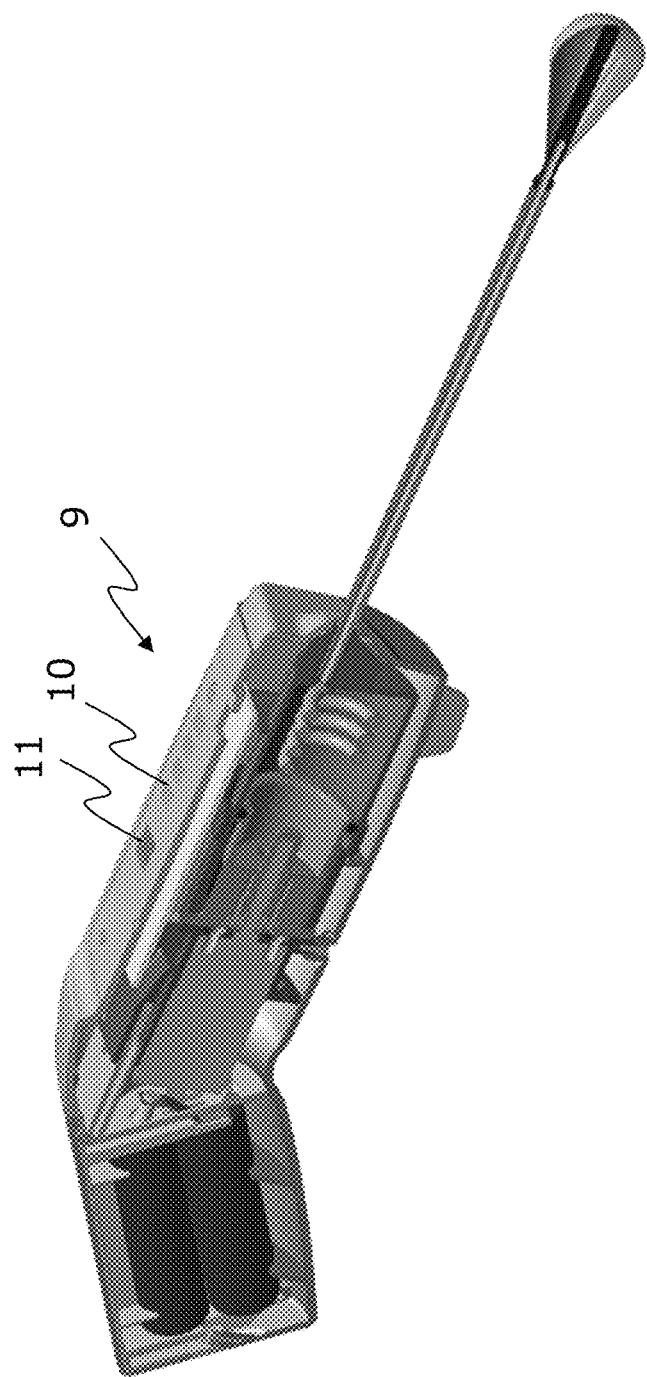
FIG. 4 illustrates details of the piston.

FIG. 4 illustrate isometric cross sectional view of the apparatus disclosing the buttons 10 for controlling operation of the apparatus and a display 11 for monitoring the temperature and/or the duration of the treatment.

The control system may particularly provide a fully automatic system managing the entire treatment, i.e. the heating of the inflation medium, the expansion of the bladder, the duration in which the bladder is expanded and the collapsing of the bladder once the treatment is finished.

The control system may be integrated in a printed circuit board (PCB) which includes memory, a computer processing unit, and a program executable in the processing unit and configured to make the control system communicate with the heating means, the motor, and/or with the sensors to carry out the processes of:
    heating the inflation medium until a predetermined temperature is achieved;
    operating the motor to control the pressure in the bladder and to inflate and deflate the bladder;
    counting a duration by a timer;
    notifying the user when the treatment is finished.

The control system may have storage means in which all data related to the treatment is stored. The control system may further have communication means adapted to provide documentation including data describing a treatment, e.g. the temperature, the duration, the pressure of the inflation medium and/or other data relevant for evaluating the treatment, e.g. the duration from the occlusion member is removed until the bladder is emptied.

Figure 5:
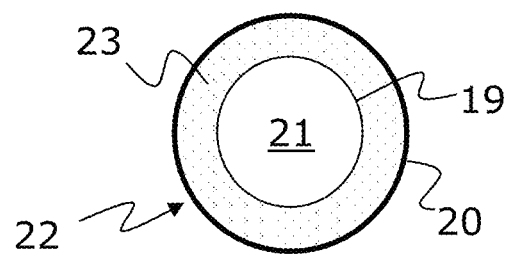
FIG. 5 illustrates details of the catheter in a cross sectional view.

FIG. 5 illustrates details of the catheter in a cross sectional view. The catheter comprises first and second coaxial elements 19, 20 extending about a conduit 21. The two elements are made from different materials and have different thermal conductivity to thereby reduce thermal spreading from the conduit to the outer surface 22 of the catheter. Between the coaxial elements 19, 20, the apparatus may comprise a third element 23 having very low thermal conductivity. In one embodiment, the coaxial elements 19, 20 are in direct contact without the third element.

Figure 6:
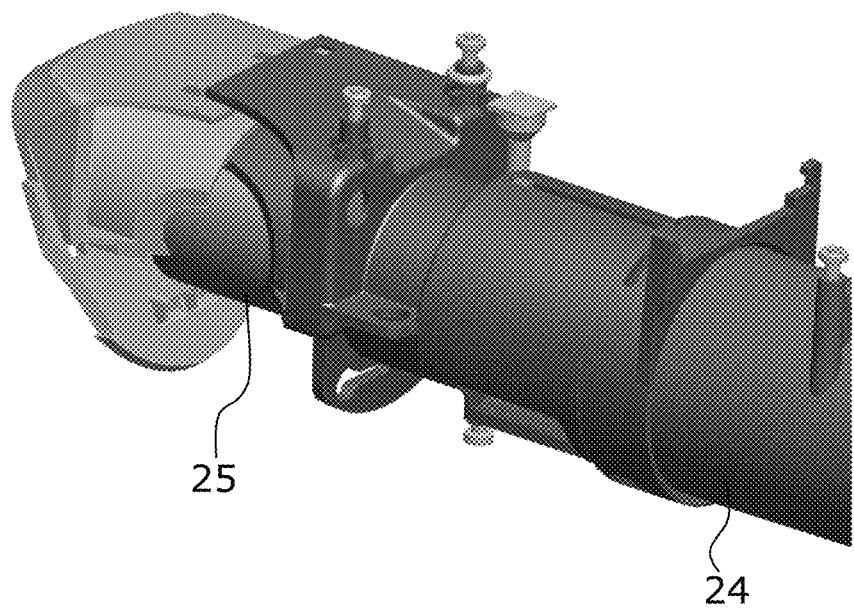
FIG. 6 illustrates details of the chamber.

FIG. 6 illustrates in a perspective view, the displacement chamber 24 and the motor 25 which constitutes the power driven means.

Figure 7:
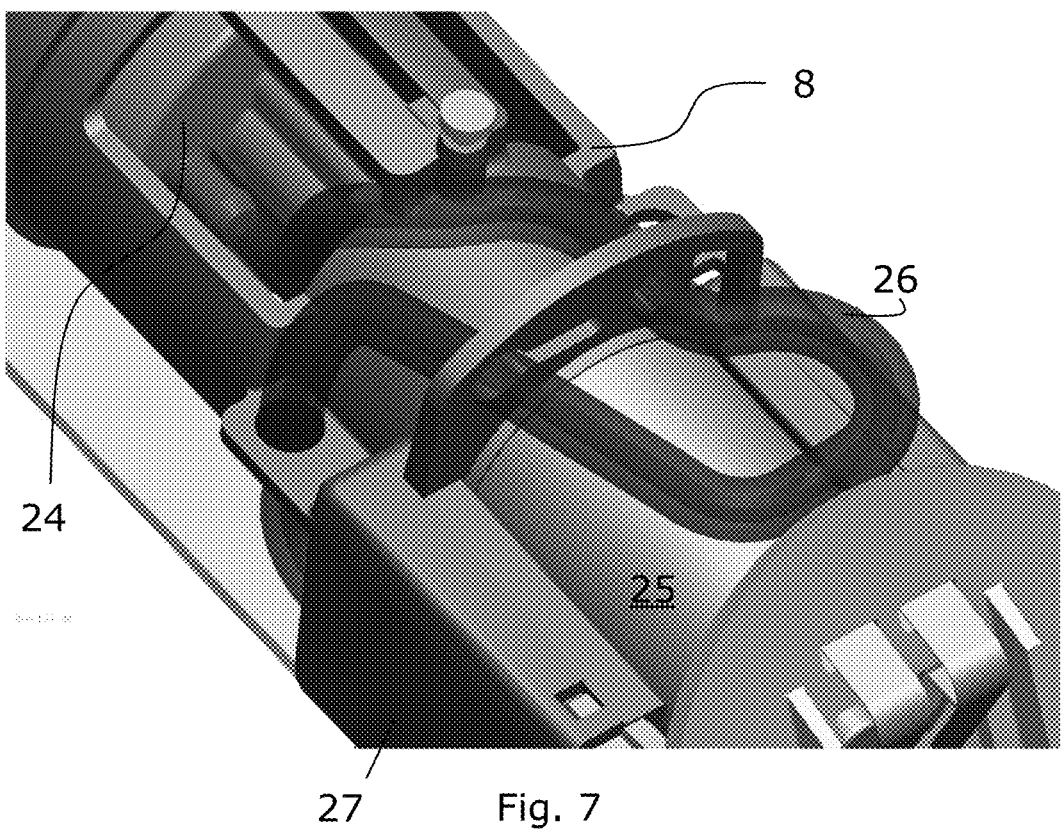
FIGS. 7 and 8 illustrate further details of the chamber.
Figure 8:
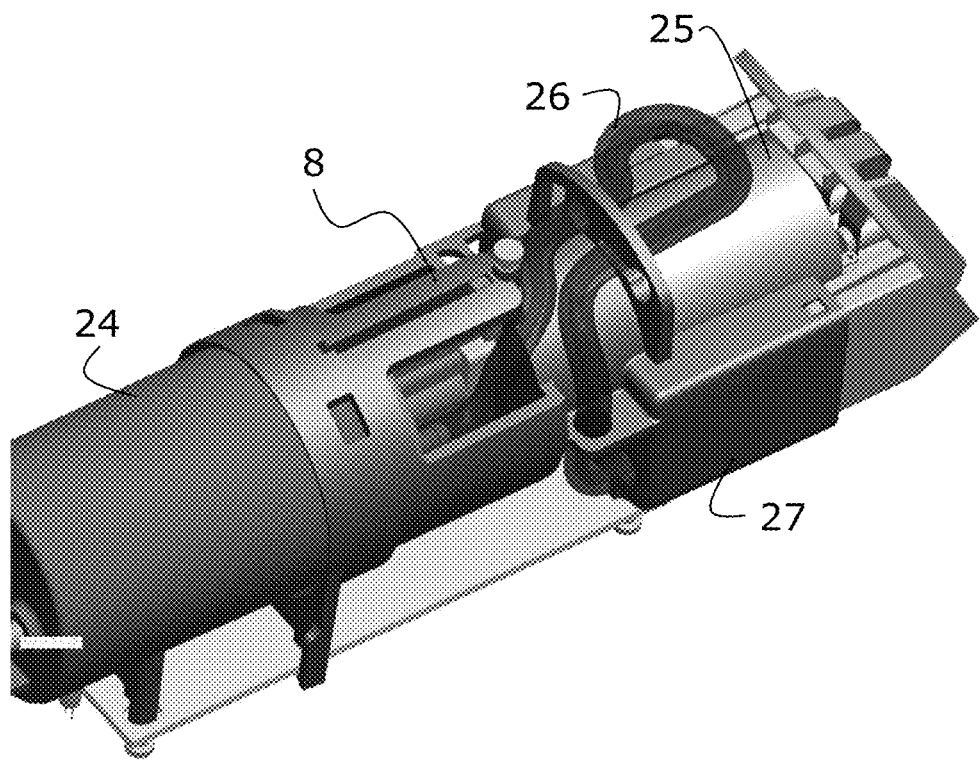

FIGS. 7 and 8 illustrate further details of the chamber 24. In this view, it is illustrated that the chamber comprises an emergency release structure 26 constituted by a rubber tube. The emergency release structure is in fluid communication with the body 27 which contains a liquid absorbing material. A valve (not shown) controls the drainage of inflation medium into the body 8. The emergency release structure is operated via the valve e.g. if the power driven means fails, e.g. when the battery is empty or in case of faults.

Figure 9:
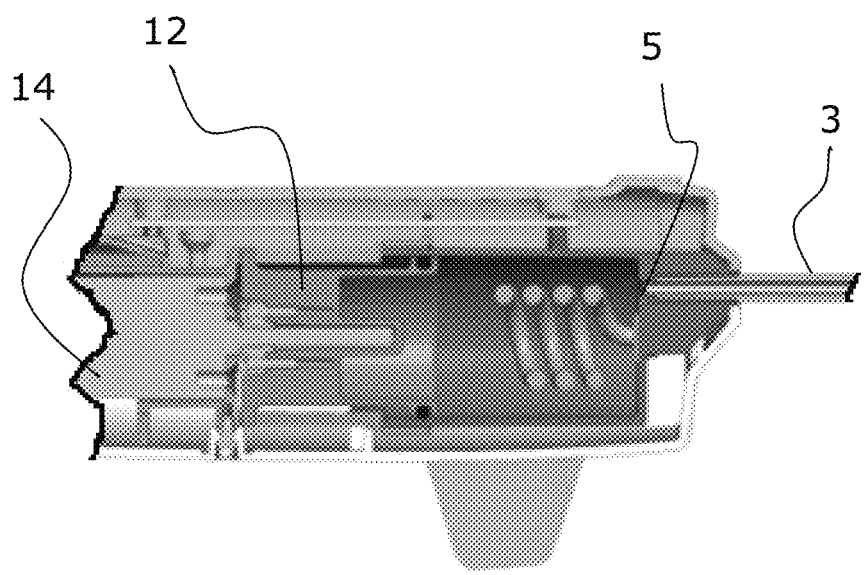
FIG. 9 illustrates a cut out section of the apparatus disclosing the chamber, the piston, and circle indicating where the occlusion member is disposed.

FIG. 9 illustrate a cut out section of the apparatus, disclosing the piston 12, the motor 14, and a section of the catheter 3, disclosing where the occlusion member 5 is disposed in the inlet to the catheter from re reservoir.

Figure 10:
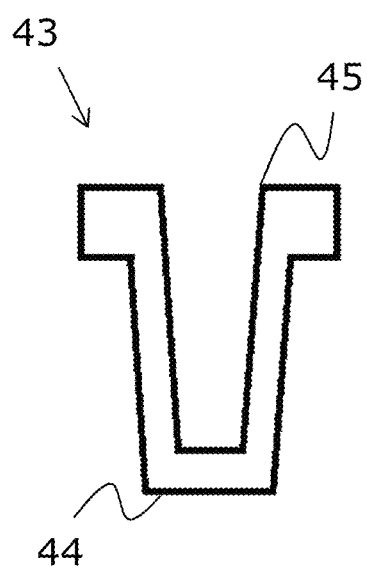
FIGS. 10 & 11 illustrate sectional views of two embodiments of the occlusion member.
Figure 11:
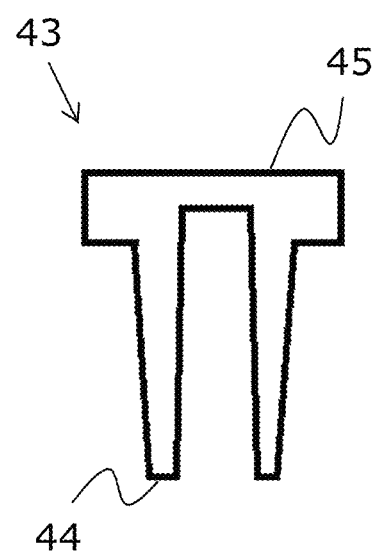

FIGS. 10-11 illustrate a cross-sectional view of the occlusion member 43. The occlusion member 43 is elongated and tapered towards on end configured to be inserted in the tube 44, the opposing end is configured with a wider section that is configured to extend into chamber 45.

FIG. 10, shows an embodiment of the occlusion member comprising a cavity extending from an open end to a closed end, where the open end is at the end facing the chamber.

FIG. 11, shows an embodiment of the occlusion member comprising a cavity extending from an open end to a closed end, where the open end is at the end facing catheter.

In use, the inflation medium can enter into the inner cavity and thereby more effectively melt the occlusion member. For this purpose, the occlusion member is arranged in the catheter with the open end 44 towards the reservoir, i.e. facing away from the bladder. The occlusion member is located close to the heating means 15 and it therefore quickly influenced by heating of the inflation medium.

Figure 12:
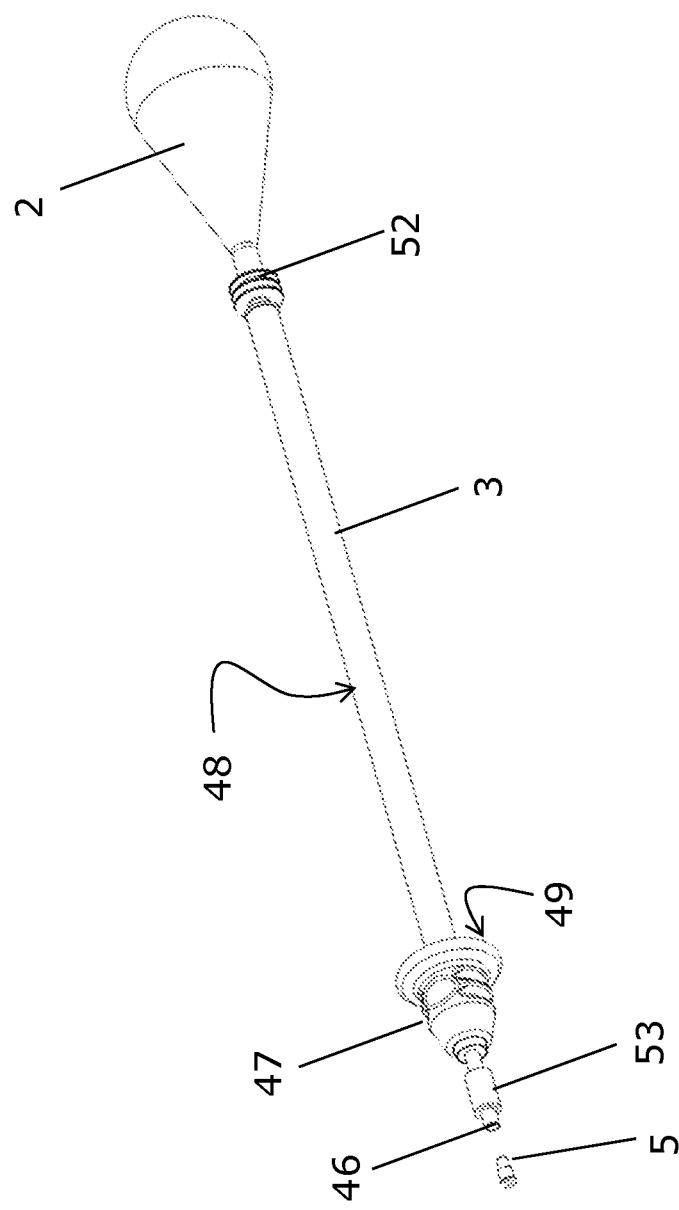
FIGS. 12 and 13 illustrate an embodiment of the catheter with an insertion stop and a sealing element.
Figure 13:
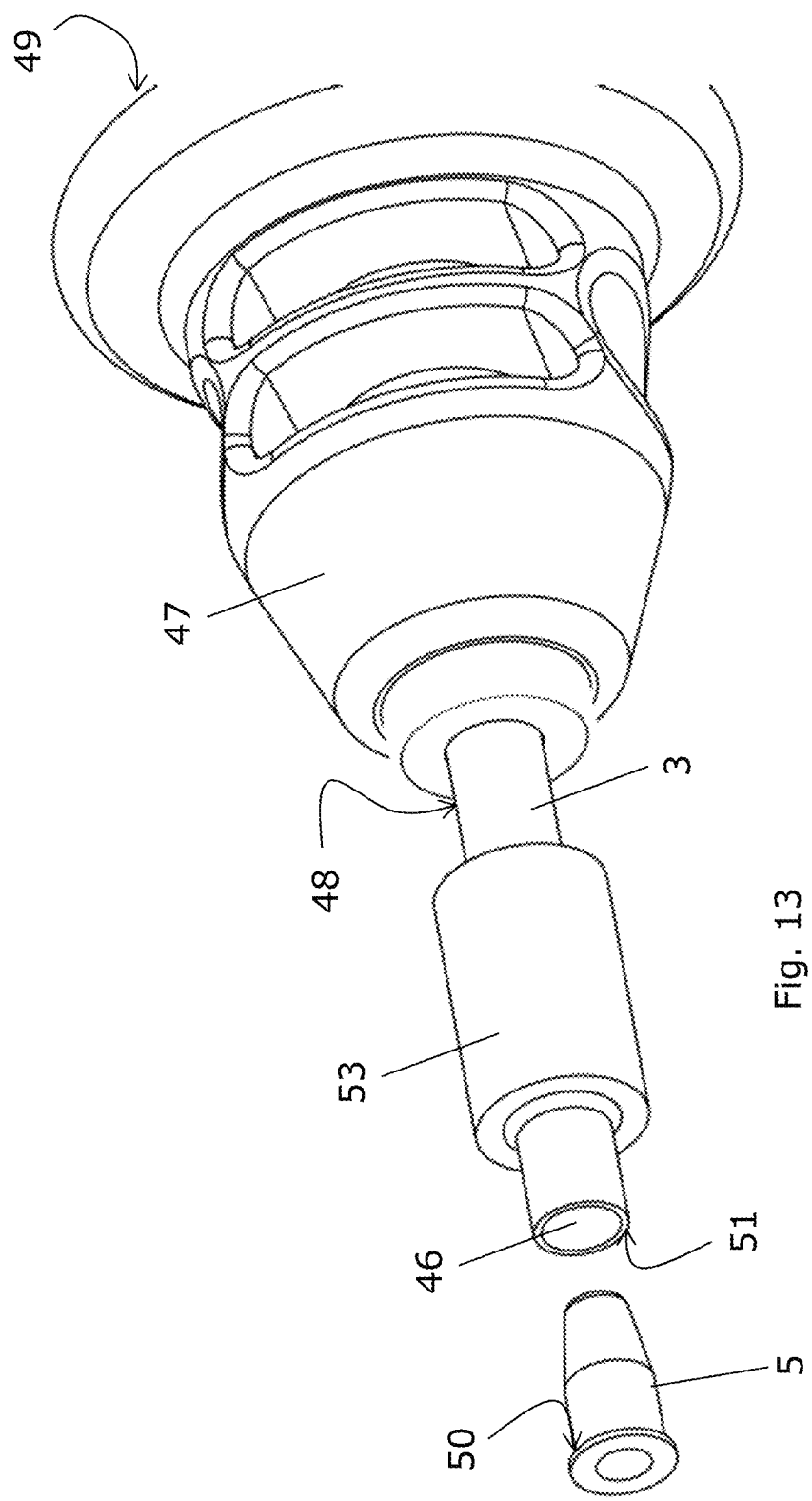

FIGS. 12 and 13 illustrate an embodiment of the catheter with an insertion stop and a sealing element.

FIG. 13 is an enlarged view of the occlusion member 5 before it is inserted into the opening 46 into the distal end of the catheter. The insertion stop 47 is an optional feature which allows improved control over the insertion depth of the catheter into the uterus. The insertion stop is slidable along the surface 48 of the catheter and can prevent a too deep insertion of the catheter by contact between the front face 49 and the bottom of cervix.

The occlusion member has a cartridge shape with a lower shoulder 50 which abuts the end face 51 of the opening 46 and prevents the occlusion member from moving into the conduit in the catheter.

The sealing element 52 is soft resilient and seals against the wall of cervix and prevents drainage through cervix during the ablation procedure.

The end stop 53 limits movement of the insertion stop beyond a specific point and thereby defines a longest insertable length of the catheter.

Numbered Embodiments

1. An apparatus for treating uterine disorders by effecting necrosis of a uterine endometrium, the apparatus comprising:

a catheter having a proximal end and a distal end;
a bladder attached to the proximal end for insertion into uterus and being distendable upon introduction of an inflation medium;
a reservoir containing the inflation medium;
heating means configured to heat the inflation medium to a necrosis temperature; and
inflation means being operative for moving the inflation medium between the storage means and the bladder;
wherein the apparatus further comprises a removable occlusion member arranged between the reservoir and the bladder to prevent flow of the inflation medium from the reservoir to the bladder.

2. An apparatus according to embodiment 1, where the occlusion member is configured to be removed at a specific temperature of the inflation medium. 3. An apparatus according to embodiment 1 or 2, where the occlusion member is configured to melt at a melting temperature which is lower than the necrosis temperature.

4. An apparatus according to embodiment 3, where the melting temperature is at least 20 degrees lower than the necrosis temperature.

5. An apparatus according to any of the preceding embodiments, and being sterilised by a process causing the apparatus to reach a sterilisation temperature, and where the melting temperature is higher than the sterilisation temperature.

6. An apparatus according to embodiment 5, where the melting temperature is at least 20 degrees higher than the sterilisation temperature.

7. An apparatus according to any of the preceding embodiments, where the occlusion member is made from a thermoplastic material.

8. An apparatus according to any of the preceding embodiments, where the occlusion member is arranged to interact with the inflation means during operation of the inflation means to thereby open a passage between the bladder and the reservoir.

9. An apparatus according to any of the preceding embodiments, where the catheter forms part of a liquid communication passage between the reservoir and the bladder, and where the occlusion member forms a separate element inserted into the passage.

10. An apparatus according to any of the preceding embodiments, where the occlusion member forms an elongated element with an inner cavity extending longitudinally from an open end to a closed end.

11. An apparatus according to any of embodiments 1-9, where the occlusion member is formed by a thin film, disposed over the fluid passage into the catheter.

12. An apparatus according to any of the preceding embodiments, where the bladder has an internal pressure which is lower than an internal pressure in the reservoir.

13. An apparatus according to any of the preceding embodiments, where the occlusion member is removable by manual activation of a control.

14. An apparatus according to any of the preceding embodiments, further comprising indication means configured to provide indication to the user when the occlusion member is removed.

15. A method of sterilising an apparatus for treating uterine disorders by effecting necrosis of a uterine endometrium, the apparatus comprising:

a catheter having a proximal end and a distal end;
a bladder attached to the proximal end for insertion into uterus and being distendable upon introduction of an inflation medium;

a reservoir containing the inflation medium;
heating means configured to heat the inflation medium to a necrosis temperature;
inflation means being operative for moving the inflation medium between the storage means and the bladder; and
an occlusion member which melts at a melting temperature which is lower than the necrosis temperature and which is arranged between the reservoir and the bladder to prevent flow of the inflation medium from the reservoir to the bladder
the method comprising the steps of sterilising the apparatus by use of a process causing the apparatus to reach a sterilisation temperature which is lower than the melting temperature.

16. A method of preparing an apparatus for carrying out tissue necrosis of a uterus of a subject, the method comprising the step of providing an apparatus according to embodiment 1, heating the inflation medium, and melting the occlusion member by use of the heated inflation medium.

17. A method of making an apparatus for treating uterine disorders by effecting necrosis of a uterine endometrium, the method comprising;
attaching a bladder to a reservoir by a catheter to thereby provide a flow passage between the reservoir and the bladder, and
arranging
a meltable occlusion member in the flow passage.

18. A method according to embodiment 17, comprising the step of providing heating means configured to heat the inflation medium to a necrosis temperature, and where the meltable occlusion member is made from an occlusion material having a melting point below the necrosis temperature.

19. A method according to any of embodiments 17-18, comprising the step of sterilising at least a part of the apparatus by a process causing the apparatus to reach an elevated sterilisation temperature and where the meltable occlusion member is made from an occlusion material having a melting point above the sterilisation temperature.

20. A method according to any of embodiments 17-19, where gas is extracted from the bladder before the occlusion member is arranged in the flow passage.

The invention claimed is:

1. An apparatus for treating uterine disorders by effecting necrosis of a uterine endometrium, the apparatus comprising:
a catheter having a proximal end and a distal end;
a bladder attached to the proximal end for insertion into uterus and being distendable upon introduction of an inflation medium;
a reservoir containing the inflation medium;
heating means configured to heat the inflation medium to a necrosis temperature; and
inflation means being operative for moving the inflation medium between the reservoir means and the bladder;
wherein the apparatus further comprises a removable occlusion member arranged between the reservoir and the bladder to prevent flow of the inflation medium from the reservoir to the bladder; wherein the occlusion member is configured to melt at a melting temperature which is lower than the necrosis temperature.

2. The apparatus according to claim 1, wherein the occlusion member is configured to be removed at a specific temperature of the inflation medium.

3. The apparatus according to claim 1, wherein the occlusion member is configured to melt at a melting temperature which is lower than the necrosis temperature.

4. The apparatus according to claim 1, being sterilised by a process causing the apparatus to reach a sterilisation temperature, and wherein the melting temperature is higher than the sterilisation temperature.

5. The apparatus according to claim 1, wherein the catheter forms part of a liquid communication passage between the reservoir and the bladder, and wherein the occlusion member forms a separate element inserted into the passage.

6. The apparatus according to claim 1, wherein the occlusion member forms an elongated element with an inner cavity extending longitudinally from an open end to a closed end.

7. The apparatus according to claim 1, wherein the bladder has an internal pressure which is lower than an internal pressure in the reservoir.

8. The apparatus according to claim 1, wherein the occlusion member is removable by manual activation of a control.

9. The apparatus according to claim 1, wherein the bladder has negative pressure until the occlusion member is removed.

10. The apparatus according to claim 1, wherein the inflation means is configured to move the inflation medium between the storage means and the bladder at a pressure which exceeds a burst pressure by which the occlusion member is removed by bursting.

11. The apparatus according to claim 1, wherein the occlusion member reduces water permeation from the bladder to the reservoir to less than 0.1 gram in 24 hours at 20 degrees Celsius.

12. A method of sterilising an apparatus for treating uterine disorders by effecting necrosis of a uterine endometrium, the apparatus comprising:
a catheter having a proximal end and a distal end;
a bladder attached to the proximal end for insertion into a uterus and being distendable upon introduction of an inflation medium;
a reservoir containing the inflation medium;
heating means configured to heat the inflation medium to a necrosis temperature;
inflation means being operative for moving the inflation medium between the reservoir means and the bladder; and
an occlusion member which melts at a melting temperature which is lower than the necrosis temperature and which is arranged between the reservoir and the bladder to prevent flow of the inflation medium from the reservoir to the bladder
the method comprising the steps of sterilising the apparatus by use of a process causing the apparatus to reach a sterilisation temperature which is lower than the melting temperature.

13. A method of preparing an apparatus for carrying out tissue necrosis of a uterus of a subject, the method comprising the step of providing an apparatus according to claim 1, heating the inflation medium, and melting the occlusion member by use of the heated inflation medium.

* * * * *